United States Patent [19]

McMichael

[11] Patent Number: 5,610,136
[45] Date of Patent: Mar. 11, 1997

[54] METHOD FOR TREATMENT OF BENIGN PROSTATIC HYPERTROPHY

[75] Inventor: John McMichael, Delanson, N.Y.

[73] Assignee: Milkhaus Laboratory, Inc., Delanson, N.Y.

[21] Appl. No.: 593,501

[22] Filed: Jan. 30, 1996

[51] Int. Cl.$^6$ ..................................................... A61K 38/24
[52] U.S. Cl. ................................................. 514/8; 514/12
[58] Field of Search ............................................ 514/8, 12

[56] References Cited

U.S. PATENT DOCUMENTS

| | | | |
|---|---|---|---|
| 4,002,738 | 1/1977 | Johnson et al. | 424/177 |
| 4,116,776 | 9/1978 | Dalbow et al. | 195/103.7 |
| 4,144,031 | 3/1979 | Acevedo et al. | 23/230 B |
| 4,201,770 | 5/1980 | Stevens | 424/177 |
| 4,228,127 | 10/1980 | Acevedo et al. | 422/61 |
| 4,302,386 | 11/1981 | Stevens | 260/112.5 R |
| 4,321,260 | 3/1982 | Auclair | 424/177 |
| 4,384,995 | 5/1983 | Stevens | 260/112.5 R |
| 4,526,716 | 7/1985 | Stevens | 260/112.5 R |
| 4,691,006 | 9/1987 | Stevens | 530/324 |
| 4,692,332 | 9/1987 | McMichael | 424/88 |

OTHER PUBLICATIONS

Acevedo et al., "Expression of Membrane–Associated Human Chorionic Gonadotrophin, Its Subunits, and Fragments by Cultured Human Cancer Cells," *Cancer*, 69:1829–1842 (1992).

Acevedo et al., "Human Chorionic Gonadotropin–Beta Subunit Gene Expression in Cultured Human Fetal and Cancer Cells of Different Types and Origins," *Cancer*, 76:1467–1475 (1995).

Fauve et al., "Antiinflammatory Effects of Murine Malignant Cells," *Proc. Nat'l Acad. Sci. USA*, 71(10):4052–4056 (Oct., 1974).

Hanna et al., "Relationship Between Metastatic Potential and Resistance to Natural Killer Cell–Mediated Cytotoxicity in Three Murine Tumor Systems," *JNCL*, 66:1183–1190 (Jun., 1981).

Imecik et al., "Diagnostic Value of Sialic Acid in Malignant Pleural Effusions," *Chest*, 102:1819–1822 (1992).

Regelson, W., Have We Found the "Definitive Cancer Biomarker"?, *Cancer*, 76(8):1299–1474 (Oct. 15, 1995).

Triozzi et al., "Clinical and Immunologic Effects of a Synthetic β–Human Chorionic Gonadotropin Vaccine," *Inter. J. Oncol.*, 5:1447–1453 (1994).

van Beek et al., "Increased Sialic Acid Density in Surface Glycoprotein of Transformed and Malignant Cell–a General Phenomeon?," *Can. Res.*, 33:2913–2922 (Nov., 1973).

*Primary Examiner*—Howard E. Schain
*Attorney, Agent, or Firm*—Marshall, O'Toole, Gerstein, Murray & Borun

[57] ABSTRACT

The present invention is directed to methods of treating benign prostatic hypertrophy comprising the step of administering to a subject suffering from benign prostatic hypertrophy a chorionic gonadotropin or a pharmaceutically active fragment or derivative thereof in an amount effective to alleviate one or more symptoms of benign prostatic hypertrophy.

6 Claims, No Drawings

METHOD FOR TREATMENT OF BENIGN PROSTATIC HYPERTROPHY

BACKGROUND OF THE INVENTION

The present invention is directed to immunotherapeutic methods for the treatment of benign prostatic hypertrophy.

Benign prostatic hypertrophy (hyperplasia) is a condition involving enlargement of the prostate gland causing variable degrees of bladder outlet obstruction. The condition is commonly seen in men over the age of 50. The etiology of the condition is unknown but may involve alterations in hormonal balance associated with aging. Multiple fibroadenomatous nodules occur in the periurethral region of the prostate gland, probably originating within the periurethral glands themselves rather than in the true fibromuscular prostate, which is displaced peripherally by progressive growth of the hyperplastic nodules. As the lumen of the prostatic urethra is compromised, the outflow of urine is progressively obstructed, with hypertrophy of the bladder detrusor, trabeculation, cellule formation, and diverticula. Incomplete bladder emptying causes stasis and predisposes to infection with secondary inflammatory changes in the bladder and the upper urinary tract. Bladder outlet obstruction symptoms include progressive urinary frequency, urgency, and nocturia due to incomplete emptying and rapid refilling of the bladder. Hesitancy and intermittency with decreased size and force of the urinary stream occur. Sensations of incomplete emptying, terminal dribbling, almost continuous overflow incontinence, or complete urinary retention may ensue.

Therapy for benign prostatic hypertrophy has been surgical with transurethral resection of the prostate (TURP) as the preferred operative procedure. Larger benign prostates may be managed by open surgery using the suprapubic or retropubic approach that permits enucleating of the adenomatous tissue from within the surgical capsule. Nevertheless, there remains a desire in the art for an effective non-surgical treatment for benign pro static hyperplasia.

U.S. Pat. No. 4,002,738 discloses the use of a luteinizing hormone releasing factor (LHRF) sometimes generically known as gonadorelin, which causes luteinizing hormone, a pituitary gonadotropin, to be released from the pituitary to treat various tumors. U.S. Pat. No. 4,321,260 discloses the use of gonadorelin in the treatment of benign prostatic hyperplasia.

McMichael, U.S. Pat. No. 4,692,332 discloses the use of equine chorionic gonadotropin and human chorionic gonadotropin in combination with an immune enhancer such as a lysate of *Staphylococcus aureus* for treatment of malignant neoplasia. The mechanism of action in the treatment of the cancer was proposed to involve chorionic gonadotropin as a signal molecule capable of inducing apoptosis via membrane changes on the transformed cell at the molecular level, or alternatively by altering the electrical charge of the transformed cell to render it more susceptible to immune elimination. This patent further taught the need to stimulate the cell mediated immune response so that necrotic debris associated with tumor reduction could be efficiently phagocytized to prevent a potentially fatal Herxheimer-type reaction. U.S. Pat. No. 4,692,332, however, fails to disclose the use of chorionic gonadotropin for treatment of non-neoplastic states such as benign prostatic hypertrophy.

SUMMARY OF THE INVENTION

The present invention is directed to immunotherapeutic methods for the treatment of benign prostatic hypertrophy and alleviation of its resulting symptoms. Specifically, the invention is directed to methods for treatment of urinary and sexual dysfunctions associated with benign prostatic hypertrophy such as nocturia, dribbling, urinary hesitation and reduced sexual activity. According to the method of the invention, benign prostatic hypertrophy is treated by the step of administering to a subject suffering from benign prostatic hypertrophy a chorionic gonadotropin or a pharmaceutically active fragment or derivative thereof in an amount effective to alleviate one or more symptoms of benign prostatic hypertrophy. Preferred chorionic gonadotropins for use according to the methods of the invention include equine and human chorionic gonadotropins with human chorionic gonadotropin (hCG) being preferred. Human chorionic gonadotropin used according to the methods of the invention is preferably obtained in the form of lyophilized powder which is derived from the urine of pregnant women as per U.S. FDA approved procedures. The lyophilized powder may then be reconstituted in any of a variety of pharmaceutically acceptable diluent with 0.9% saline being preferred.

The compositions are preferably administered as sublingual drops in dosages ranging from about 0.2 International Units to 20 International Units with dosages of about 2 International Units of human chorionic gonadotropin per dosage four times daily being preferred as the initial treatment dosage. After an initial therapeutic effect has been noted, preferred dosages comprise about 2 International Units of human chorionic gonadotropin per dosage once or twice daily. While the compositions of the invention are preferably administered as sublingual drops, it is contemplated that they may be administered by other means known to the art including by injection and transdermal administration. When administered in the form of sublingual drops, the compositions preferably comprise single drops (approximately 0.05 ml) of hCG at a concentration of 40 International Units per mL in 0.9% saline.

Without being bound by a theory of the invention, it is believed that chorionic gonadotropins are useful in treatment of benign prostatic hypertrophy because although that condition represents a non-neoplastic form of cell growth, the cell growth is disorganized and somewhat resembles tumor growth. It is further believed that human chorionic gonadotropin can act as a signal molecule to induce the restoration of homeostatic control of growth for benign cells.

In the methods of the invention, an immune enhancer is not required because the massive cell die-off that could cause a Herxheimer-type reaction does not occur. Chorionic gonadotropin is used in relatively low concentrations as a signal to restore normal control of cell growth and thus reverse the hyperplastic state. With reversal of the hyperplastic state, pressure on the ureter and bladder is reduced and symptoms including nocturia, dribbling, urinary hesitation and reduced sexual activity are alleviated.

DETAILED DESCRIPTION OF THE INVENTION

The examples presented below illustrate practice of embodiments of the methods of the invention.

EXAMPLE 1

In this example, an 85 year old male presented with a ten year history of prostate hyperplasia manifested by urinary hesitation with terminal dribbling. The urinary stream was estimated to be reduced to one-fourth of its original volume.

The subject was treated by sublingual administration four times daily of one drop (0.05 mL) of a formulation comprising 2 International Units of human chorionic gonadotropin in 0.9% saline. After four weeks the subject's urinary stream had increased in volume 30% and terminal dribbling had nearly been eliminated with no adverse side effects.

EXAMPLE 2

In this example, a 71 year old male presented with a history of several years of slower stream, hesitation and occasional terminal dribbling. The patient suffered from nocturia, voiding twice nightly. The subject also had to stand to void completely as he experienced difficulty emptying his bladder if sitting on a commode. The subject was treated with the formulation of Example 1 comprising 2 International Units of human chorionic gonadotropin sublingually four times daily. After four weeks the subject showed improvement with the result that nocturia had been eliminated and dribbling was reduced although flow volume had not increased.

EXAMPLE 3

In this example, a 71 year old male presented with a history for several years of arising at 5 to 6 AM to void and urinary frequency in the morning every 15 minutes to 1 hour. The subject dribbles post-voiding thus staining his underwear and suffers from an erectile disfunction. The subject was treated with the formulation of Example 1 comprising 2 International Units of human chorionic gonadotropin sublingually four times daily. After four weeks the subject still gets up at 5 to 6 AM to void and has the same urinary frequency, but post-voiding dribbling has nearly been eliminated.

EXAMPLE 4

In this example, a 77 year old male presented with recent symptoms of benign prostate hyperplasia including voiding every 30 minutes to 2 hours and nocturia three times nightly. The subject was treated with the formulation of Example 1 comprising 2 International Units of human chorionic gonadotropin sublingually four times daily. After four weeks, the subject did not exhibit any response.

EXAMPLE 5

In this example, a 71 year old male presented with a history of benign prostatic hypertrophy for two years including a mild delay at the start of urination, symptoms of nocturia 2 or 3 times nightly and hesitation at the end of urination. The subject was able to rub his back and void an additional 16 ounces of urine, otherwise he suffered from terminal dribbling. The subject was treated with the formulation of Example 1 comprising 2 International Units of human chorionic gonadotropin and sublingually four times daily. After four weeks nocturia was reduced to zero to twice nightly and hesitation and terminal dribbling have improved. In addition, at the end of urination and rubbing his back, the subject voids only about 8 ounces which suggests better bladder emptying.

EXAMPLE 6

In this example, a 60 year old male presented with a two year history of urinary hesitation every morning with erectile dysfunction. The subject was treated with the formulation of Example 1 comprising 2 International Units of human chorionic gonadotropin sublingually four times daily. After four weeks hesitation was much improved and the subject voided larger amounts. Erectile function also improved even though the subject had not responded to testosterone injections prior to being administered the therapy of the invention.

EXAMPLE 7

In this example, a 74 year old male presented with a three year history of symptoms following transurethral resection of the prostate (TURP) surgery. Specifically, the subject exhibited urinary frequency of 12 to 14 times during the day and one or two times at night. The subject had engaged in no sexual activity since the TURP surgery as he had no desire and was impotent. The subject was treated with the formulation of Example 1 comprising 2 International Units of human chorionic gonadotropin sublingually four times daily. After four weeks urinary frequency was reduced to nine times during the day and once at night and the subject was sexually active again with an increase in sexual desire. Prior to treatment according to the invention, the subject had a subjective score of 0 on a scale of 10 for sexual activity. After treatment, the subject self-evaluated himself with a score of 5 on a scale of 10.

EXAMPLE 8

In this example, a 71 year old male subject presented with a history of nocturia 1 to 3 times nightly and urinary frequency six times during the day with dribbling. The subject was treated with the formulation of Example 1 comprising 2 International Units of human chorionic gonadotropin sublingually four times daily. After four weeks the subject reported an increase in stream, decrease in nocturia to one time or less nightly and a decrease in urinary frequency to four times daily with a decrease in dribbling. The subject also reported having sexual activity for the first time in two to three years.

Numerous modifications and variations of the above-described invention are expected to occur to those of skill in the art. Accordingly, only such limitations as appear in the appended claims should be placed thereon.

What is claimed is:

1. A method for the treatment of benign prostatic hypertrophy comprising the step of:
    administering to a subject suffering from benign prostatic hypertrophy a chorionic gonadotropin or a pharmaceutically active fragment or derivative thereof in an amount effective to alleviate one or more symptoms of benign prostatic hypertrophy.

2. The method of claim 1 wherein the chorionic gonadotropin is selected from the group consisting of human and equine chorionic gonadotropins.

3. The method of claim 2 wherein the chorionic gonadotropin is human chorionic gonadotropin.

4. The method of claim 1 wherein the chorionic gonadotropin is administered in a dosage ranging from 0.2 International Units to 20 International Units.

5. The method of claim 1 wherein the chorionic gonadotropin dosage is administered from one to four times daily.

6. The method of claim 1 wherein the dosage is administered in the form of sublingual drops.

* * * * *